(12) United States Patent
Hölzl et al.

(10) Patent No.: US 7,078,550 B2
(45) Date of Patent: Jul. 18, 2006

(54) SILANYL PHENOLS AND NAPHTHOLS

(75) Inventors: Werner Hölzl, Eschentzwiller (FR); Wolfgang Haap, Lörrach (DE); Jürgen Koppold, Lörrach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 75 days.

(21) Appl. No.: 10/466,460

(22) PCT Filed: Jan. 10, 2002

(86) PCT No.: PCT/EP02/00192

§ 371 (c)(1),
(2), (4) Date: Jul. 15, 2003

(87) PCT Pub. No.: WO02/058016

PCT Pub. Date: Jul. 25, 2002

(65) Prior Publication Data
US 2004/0058891 A1    Mar. 25, 2004

(30) Foreign Application Priority Data
Jan. 18, 2001  (EP) ................................. 01810050

(51) Int. Cl.
*C07F 7/04* (2006.01)
(52) U.S. Cl. ...................... 556/449; 556/465
(58) Field of Classification Search ............... 556/449, 556/465
See application file for complete search history.

(56) References Cited

U.S. PATENT DOCUMENTS

| | | | |
|---|---|---|---|
| 3,705,075 A | 12/1972 | Marzocchi | 161/176 |
| 5,063,134 A | 11/1991 | Horiguchi et al. | 430/192 |
| 5,756,485 A | 5/1998 | Richard et al. | 514/63 |

FOREIGN PATENT DOCUMENTS

| | | | |
|---|---|---|---|
| DE | 1812951 | | 7/1969 |
| DE | 3810247 | | 10/1988 |
| EP | 0385732 | | 9/1990 |
| EP | 0412407 | | 2/1991 |
| EP | 0796861 | | 9/1997 |
| EP | 0846683 | | 6/1998 |
| JP | 02 078 688 | * | 3/1990 |
| JP | 1988-227860 | A2 * | 3/1990 |
| JP | 1989-6299 | A2 * | 7/1990 |
| WO | 92/03288 | | 3/1992 |

OTHER PUBLICATIONS

John McMurry, Organic Chemistry Textbook, 3rd Edition, p. 1023, 1992.*
Chemical Abstracts vol. 124, No. 2, No. 10139 (1996) for JP 07196804.
Chemical Abstracts vol. 117, No. 20, No. 201937 (1992) for JP 03289659.
Bruce et al., J. Chem. Soc., Perkin Trans. 1 (1981), (10), pp. 2677-2679.
English abstract for EP 0412407 (1991).
Derwent Abstract 1967-06212H for DE 1812951 (1969).

* cited by examiner

*Primary Examiner*—Johann Richter
*Assistant Examiner*—Chukwuma Nwaonicha
(74) *Attorney, Agent, or Firm*—Kevin T. Mansfield

(57) ABSTRACT

There are described silanyl phenols and naphthols of formula (1a) or (1b), wherein $R_1$ is hydrogen; halogen; hydroxy; $C_1$–$C_{20}$alkyl; $C_3$–$C_{12}$cycloalkyl; $C_1$–$C_{20}$alkoxy; trifluoromethyl; pentafluoroethyl; mono- or di-$C_1$–$C_5$alkylamino; hydroxy-$C_1$–$C_5$alkyl; or phenyl, phenyl-$C_1$–$C_{20}$alkyl, phenoxy, phenyl-$C_1$–$C_{20}$alkoxy, naphthyl or naphthyl-$C_1$–$C_{20}$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro; $R_2$, $R_3$ and $R_4$ are each independently of the others hydrogen; $C_1$–$C_{20}$alkyl; or $C_3$–$C_{12}$-cycloalkyl; $R_5$, $R_6$ and $R_7$ are each independently of the others $C_1$–$C_{20}$alkyl, $C_5$–$C_{10}$aryl, $C_1$–$C_{20}$alkoxy, phenyl-$C_1$–$C_{20}$alkyl, phenyl-$C_1$–$C_{20}$alkoxy, $C_2$–$C_5$alkenyl, —O—Si—$(C_1$–$C_5$alkyl)$_3$; or O—Si—$(C_1$–$C_5$alkyl)$_2$-O—Si$(C_1$–$C_5$alkyl)$_3$ and n is 0 or 1. The compounds exhibit a pronounced activity against Gram positive and Gram negative bacteria, and also against yeasts and moulds

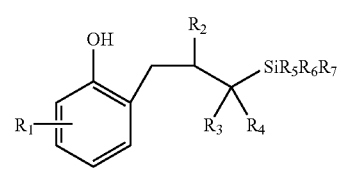

(1a)

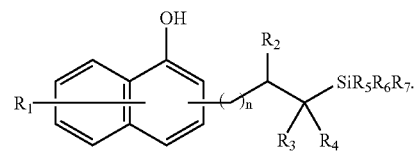

(1b)

11 Claims, No Drawings

SILANYL PHENOLS AND NAPHTHOLS

The present invention relates to selected silanyl phenols and naphthols, to the preparation of such compounds, to the use of such compounds for the antimicrobial treatment of surfaces, as antimicrobial active ingredients against Gram-positive and Gram-negative bacteria, yeasts and fungi and in the preservation of cosmetics, household products, textiles, plastics, and for use in disinfectants.

The compounds according to the invention correspond to the formula

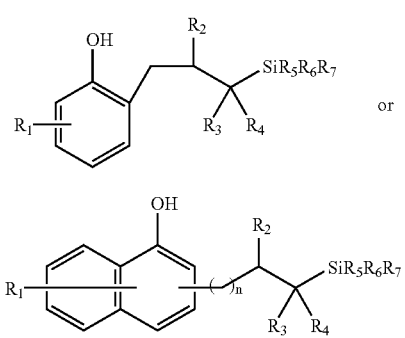

wherein
$R_1$ is hydrogen; halogen; hydroxy; $C_1$–$C_{20}$alkyl; $C_3$–$C_{12}$cycloalkyl; $C_1$–$C_{20}$alkoxy; trifluoromethyl pentafluoroethyl; mono- or di-$C_1$–$C_5$alkylamino; hydroxy-$C_1$–$C_5$alkyl; or phenyl, phenyl-$C_1$–$C_{20}$alkyl, phenoxy, phenyl-$C_1$–$C_{20}$alkoxy, naphthyl or naphthyl-$C_1$–$C_{20}$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro;

$R_2$, $R_3$ and $R_4$ are each independently of the others hydrogen; $C_1$–$C_{20}$alkyl; or $C_3$–$C_{12}$-cycloalkyl;

$R_5$, $R_6$ and $R_7$ are each independently of the others $C_1$–$C_{20}$alkyl, $C_5$–$C_{10}$aryl, $C_1$–$C_{20}$alkoxy, phenyl-$C_1$–$C_{20}$alkyl, phenyl-$C_1$–$C_{20}$alkoxy, $C_2$–$C_5$alkenyl, —O—Si—$(C_1$–$C_5$alkyl$)_3$; or —O—Si—$(C_1$–$C_5$alkyl$)_2$-O—Si$(C_1$–$C_5$alkyl$)_3$ and n is 0 or 1, there not being included compounds of formula (1a) wherein $R_1$, $R_2$, $R_3$ and $R_4$ are hydrogen and $R_5$, $R_6$ and $R_7$ are simultaneously methyl.

$C_1$–$C_{20}$Alkyl denotes straight-chain or branched alkyl radicals, e.g. methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_1$–$C_{20}$Alkoxy denotes straight-chain or branched radicals, e.g. methoxy, ethoxy, propoxy, butoxy, pentyloxy, hexyloxy, heptyloxy, octyloxy, isooctyloxy, nonyloxy, decyloxy, undecyloxy, dodecyloxy, tetradecyloxy, pentadecyloxy, hexadecyloxy, heptadecyloxy, octadecyloxy or eicosyloxy.

$C_3$–$C_{12}$Cycloalkyl denotes e.g. cyclopropyl, cyclobutyl, cyclopentyl, cycloheptyl, cyclooctyl, cyclononyl, cyclodecyl, cycloundecyl, cyclodocecyl and especially cyclohexyl.

In the context of the definitions given, alkenyl includes inter alia vinyl, allyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_5$-$C_{10}$Aryl denotes phenyl or naphthyl.

Preference is given to compounds of formula (1a) or (1b), wherein
$R_1$ is hydrogen; $C_1$–$C_{20}$alkyl; $C_1$–$C_{20}$alkoxy; or phenyl, phenoxy, phenyl-$C_1$–$C_{20}$alkyl, phenyl-$C_1$–$C_{20}$alkoxy, naphthyl or naphthyl-$C_1$–$C_{20}$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, oxo, carboxy, carboxy-$C_3$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro.

Especially preferred compounds of formula (1a) or (1b) are those wherein
$R_1$ is hydrogen, $C_1$–$C_{20}$alkyl, $C_1$–$C_{20}$alkoxy, phenyl, or phenoxy unsubstituted or substituted by halogen, $C_1$–$C_5$alkyl or by cyclo-$C_5$–$C_7$alkyl;

and especially those wherein
$R_1$ is hydrogen; $C_1$–$C_{20}$alkyl; $C_1$–$C_5$alkoxy; phenyl or phenoxy.

$R_2$, $R_3$ and $R_4$ in formula (1 a) or (1b) are preferably each independently of the others hydrogen or methyl.

$R_5$, $R_6$ and $R_7$ are preferably each independently of the others hydrogen; $C_1$–$C_{20}$alkyl; $C_1$–$C_{20}$alkoxy; $C_2$–$C_5$alkenyl; $C_6$–$C_{10}$aryl; —O—Si$(C_1$–$C_5$alkyl$)_2$-O—Si$(C_1$–$C_5$alkyl$)_3$ or —O—Si—$(C_1$–$C_5$alkyl$)_3$; and especially $C_1$–$C_5$alkyl; $C_1$–$C_{20}$alkoxy; phenyl; —O—Si$(C_1$–$C_5$alkyl$)_2$-O—Si$(C_1$–$C_5$alkyl$)_3$ or —O—Si—$(C_1$–$C_5$alkyl$)_3$.

Very special preference is given to compounds of formulae

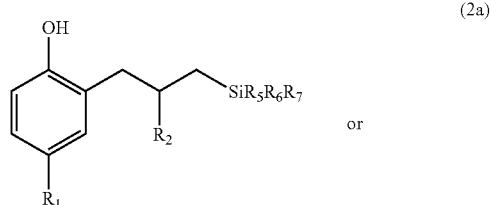

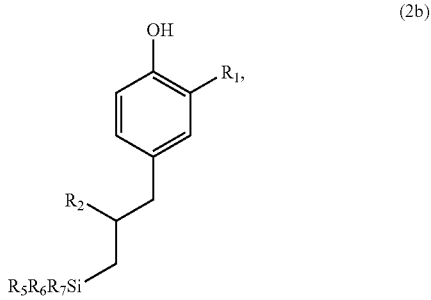

wherin
$R_1$ is hydrogen; $C_3$–$C_{20}$alkyl; $C_1$–$C_5$alkoxy; phenyl; or phenoxy, $R_2$ is hydrogen; or $C_1$–$C_5$alkyl; and $R_5$, $R_6$ and $R_7$ are each independently of the others $C_1$–$C_5$alkyl; phenyl; —O—Si$(C_1$–$C_5$alkyl$)_2$-O—Si$(C_1$–$C_5$alkyl$)_3$; or —O—Si—$(C_1$–$C_5$alkyl$)_3$.

Examples of very especially preferred compounds of the invention correspond to the formulae

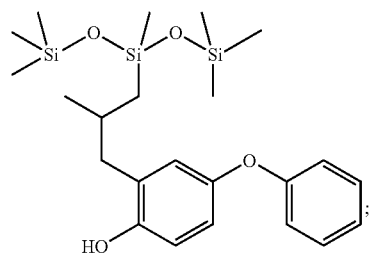
(3)

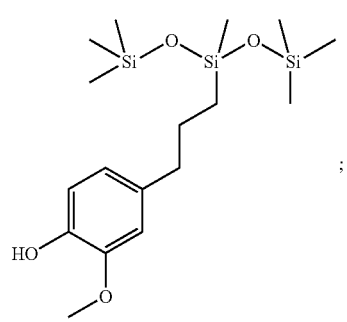
(4)

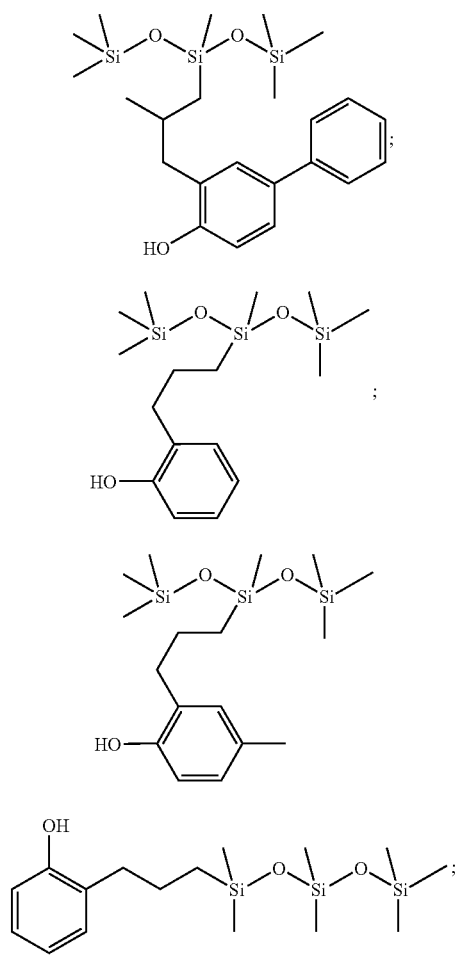
(5); (6); (7); (8)

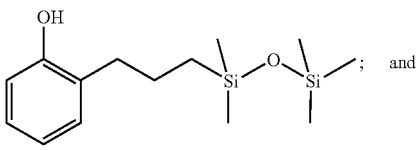
(9); and

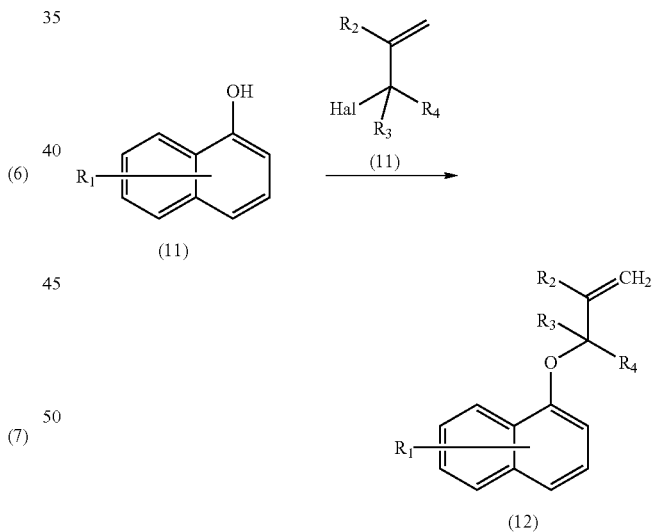
(10)

The compounds according to the invention are prepared in very general terms by the addition of silanes that contain at least one Si—H bond to phenols or naphthols substituted as desired that have unsaturated side chains (hydrosilylation).

The invention relates also to the process for the preparation of silanyl phenols and naphthols of formulae (1a) and (1b). In the process a phenol or naphthol compound is etherified with an allyl halide (1st step), the resulting alkenyl phenyl ether compound is rearranged to form an alkenylphenyl compound (2nd step), and a silane compound that contains at least one Si—H bond is added to that compound (3rd step) according to the following Scheme:

1st step:

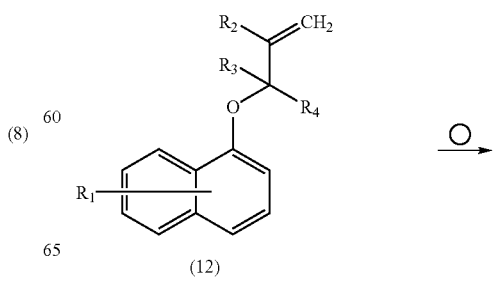

2nd step:

-continued

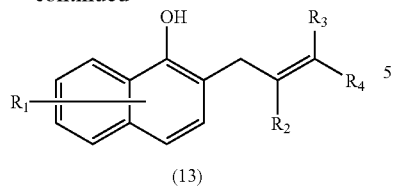

3rd step:

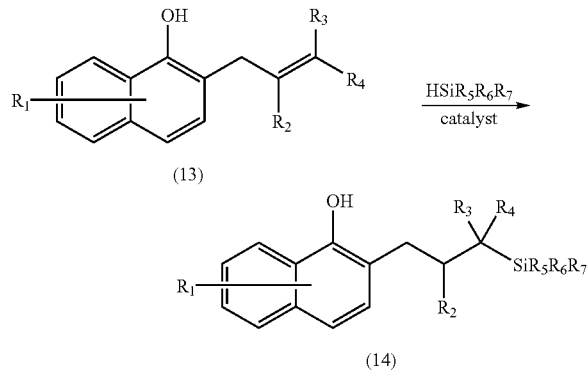

In that reaction scheme
$R_1$ is hydrogen; halogen; hydroxy; $C_1$–$C_{20}$alkyl; $C_3$–$C_{12}$cycloalkyl; $C_1$–$C_{20}$alkoxy; trifluoromethyl; pentafluoroethyl; mono- or di-$C_1$–$C_6$alkylamino; hydroxy-$C_1$–$C_5$alkyl; or phenyl, phenyl-$C_1$–$C_{20}$alkyl, phenoxy, phenyl-$C_1$–$C_{20}$alkoxy, naphthyl or naphthyl-$C_1$–$C_{20}$alkyl, each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro;
$R_2$, $R_3$ and $R_4$ are each independently of the others hydrogen; $C_1$–$C_{20}$alkyl; or $C_3$–$C_{12}$-cycloalkyl; and
$R_5$, $R_6$ and $R_7$ are each independently of the others $C_1$–$C_{20}$alkyl; $C_5$–$C_{10}$aryl; $C_1$–$C_{20}$alkoxy; phenyl-$C_1$–$C_{20}$alkyl; phenyl-$C_1$–$C_{20}$alkoxy; $C_2$–$C_5$alkenyl; —O—Si—($C_1$–$C_5$alkyl)$_3$; or —O—Si—($C_1$–$C_5$alkyl)$_2$-O—Si($C_1$–$C_5$alkyl)$_3$.

The hydrosilylation is carried out according to processes known per se in an inert organic solvent, preferably at elevated temperature, in the presence of catalytic amounts of a transition metal complex. Suitable complexes are, for example, generally complexes of the metals rhodium, iridium or cobalt, or especially carbonyls of the metals iron, cobalt, nickel, rhodium, ruthenium, manganese or chromium. Special preference is given to complexes of platinum or hexachloroplafinic acid $H_2PtCl_6$.

As starting compounds for the hydrosilylaton there are used alkenyl-phenols or -naphthols, which are prepared according to processes known per se, as described, for example, in Synthesis 1981, 310 for Friedel-Crafts allylation of phenols. The alkenyl-phenols or -naphthols are preferably prepared from readily obtainable alkenyl phenyl ethers by a Claisen rearrangement. The rearrangement reaction can be carried out with or without high-boiling solvents at temperatures of 200–250° C. The rearrangement is preferably carried out in ethylene glycol or its oligomers, or ethers thereof, especially in diethylene glycol dimethyl ether at 220° C. in a pressurised vessel. That procedure results in an especially pure reaction product.

The Invention relates also to compounds of formula

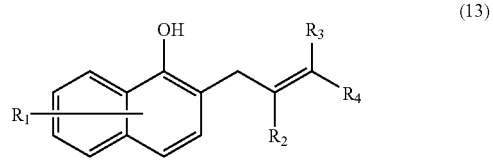

wherein
$R_1$ is hydrogen; halogen; hydroxy; $C_1$–$C_{20}$alkyl; $C_3$–$C_{12}$cycloalkyl; $C_1$–$C_{20}$alkoxy; trifluoromethyl; pentafluoroethyl; di-$C_1$–$C_5$alkylamino; hydroxy-$C_1$–$C_5$alkyl; or phenyl, phenoxy, phenyl-$C_1$–$C_{20}$alkyl, phenyl-$C_1$–$C_{20}$alkoxy, naphthyl or naphthyl-$C_1$–$C_{20}$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro;
$R_2$, $R_3$ and $R_4$ are each independently of the others hydrogen; $C_1$–$C_{20}$alkyl; or $C_3$–$C_{12}$-cycloalkyl.

Silanyl phenols and naphthols of formula

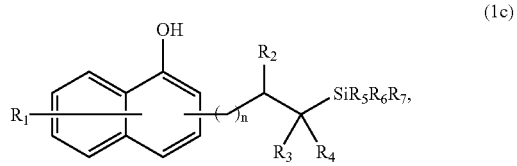

wherein
$R_1$ is hydrogen; halogen; hydroxy; $C_1$–$C_{20}$alkyl; $C_3$–$C_{12}$cycloalkyl; $C_1$–$C_{20}$alkoxy; trifluoromethyl; pentafluoroethyl; mono- or di-$C_1$–$C_5$alkylamino; hydroxy-$C_1$–$C_5$alkyl; or phenyl, phenyl-$C_1$–$C_{20}$alkyl, phenoxy, phenyl-$C_1$–$C_{20}$alkoxy, naphthyl or naphthyl-$C_1$–$C_{20}$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro;
$R_2$, $R_3$ and $R_4$ are each independently of the others hydrogen; $C_1$–$C_{20}$alkyl; or $C_3$–$C_{12}$cycloalkyl;
$R_5$, $R_6$ and $R_7$ are each independently of the others $C_1$–$C_{20}$alkyl, $C_5$–$C_{10}$aryl, $C_1$–$C_{20}$alkoxy, phenyl-$C_1$–$C_{20}$alkyl, phenyl-$C_1$–$C_{20}$alkoxy, $C_2$–$C_5$alkenyl, —O—Si—($C_1$–$C_5$alkyl)$_3$; or —O—Si—($C_1$–$C_5$alkyl)$_2$-O—Si($C_1$–$C_5$alkyl)$_3$ and
n is 0 or 1, exhibit pronounced antimicrobial activity, especially against Gram-positive and Gram-negative bacteria and against bacteria of skin flora, and also against yeasts and moulds. They are accordingly especially suitable in the disinfection, deodorisation and general and anti-microbial treatment of the skin and mucosa and of integumentary appendages (hair), more especially in the disinfection of hands and of wounds.

They are therefore suitable as antimicrobial active ingredients and as preservatives in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention accordingly relates also to a personal care preparation comprising at least one compound of formula (1c) and cosmetically tolerable carriers or adjuvants.

The personal care preparation according to the invention comprises from 0.01 to 15% by weight, preferably from 0.1 to 10% by weight, based on the total weight of the composition, of the compound of formula (1c), and cosmetically tolerable adjuvants.

Depending on the form of the personal care preparation, it will comprise, in addition to the silanyl phenol or naphthol of formula (1c), further constituents, for example sequestering agents, colourings, perfume oils, thickening or solidifying agents (consistency regulators), emollients, UV absorbers, skin-protective agents, antioxidants, additives that improve mechanical properties, such as dicarboxylic acids and/or Al, Zn, Ca and Mg salts of $C_{14}$–$C_{22}$-fatty acids, and optionally preservatives.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion the cosmetically tolerable adjuvant preferably comprises from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. For example, the following preparations especially come into consideration:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipstick, lip gloss or lip contour pencils, nail-care preparations, such as nail varnish, nail varnish remover, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams, oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams, gels, pre-shave preparations for dry shaving, aftershaves or aftershave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hair sprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:

0.01 to 5% by weight of the compound of formula (1c), 0.3 to 1% by weight titanium dioxide, 1 to 10% by weight stearic acid, ad 100% soap base, e.g. the sodium salts of tallow fatty acid and coconut fatty acid or glycerols.

A shampoo has, for example, the following composition:

0.01 to 5% by weight of the compound of formula (1c), 12.0% by weight sodium laureth-2-sulfate, 4.0% by weight cocamidopropyl betaine, 3.0% by weight NaCl and water ad 100%.

A deodorant has, for example, the following composition:

0.01 to 5% by weight of the compound of formula (1c),

60% by weight ethanol, 0.3% by weight perfume oil, and water ad 100%.

The invention relates also to an oral composition, comprising 0.01 to 15% by weight, based on the total weight of the composition, of the compound of formula (1c), and orally tolerable adjuvants.

Example of an oral composition:
1.0% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1c), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The silanyl phenols and naphthols of formula (1c) according to the invention are also suitable for the treatment, especially preservation, of textile fibre materials. Such materials are undyed and dyed or printed fibre materials, e.g. of silk, wool, polyamide or polyurethanes, and especially cellulosic fibre materials of all kinds. Such fibre materials are, for example, natural cellulosic fibres, such as cotton, linen, jute and hemp, as well as cellulose and regenerated cellulose. Preferred suitable textile fibre materials are made of cotton.

The silanyl phenols and naphthols according to the invention are also suitable for the treatment of plastics, especially for imparting antimicrobial properties to or preserving plastics, e.g. polyethylene, polypropylene, polyurethane, polyester, polyamide, polycarbonate, latex etc. Fields of use therefore are, for example, floor coverings, plastics coatings, plastics container and packaging materials; kitchen and bathroom utensils (e.g. brushes, shower curtains; sponges, bathmats), latex, filter materials (air and water filters), plastics articles used in the field of medicine, e.g. dressing materials, syringes, catheters etc., so-called "medical devices", gloves and mattresses.

Paper, for example papers used for hygiene purposes, may also be provided with antimicrobial properties using the silanyl phenols and naphthols according to the invention.

It is also possible for nonwovens, e.g. nappies/diapers, sanitary towels, panty liners, and cloths for hygiene and household uses, to be provided with antimicrobial properties in accordance with the invention.

The silanyl phenols and naphthols of formula (1c) are also used in washing and cleaning formulations, e.g. in liquid and powder detergents or fabric conditioners.

The silanyl phenols and naphthols of formula (1c) can be used especially also in household and all-purpose cleaners for cleaning and disinfecting hard surfaces.

A cleaning preparation has, for example, the following composition:
0.01 to 5% of the compound of formula (1c)

| | |
|---|---|
| 3.0% | octyl alcohol 4E0 |
| 1.3% | fatty alcohol $C_8$–$C_{10}$polyglucoside |
| 3.0% | isopropanol |
| ad 100% | water. |

In addition to preserving cosmetics and household products, it is also possible for technical products to be preserved and provided with antimicrobial properties; use as a biocide in technical processes is also possible, for example in paper treatment, especially in paper treatment liquors, printing thickeners of starch or cellulose derivatives, varnishes and paints.

The silanyl phenols and naphthols of formula (1c) are also suitable for the antimicrobial treatment of wood and for the antimicrobial treatment of leather, the preservation of leather and the provision of leather with antimicrobial properties.

The compounds according to the invention are also suitable for the protection of cosmetic products and household products from microbial damage.

The following Examples illustrate, but do not limit, the present invention.

PREPARATION EXAMPLES

The preparation of allylphenols in diethylene glycol dimethyl ether is described in general and the preparation of 2-methallyl-4-phenyl-phenol (101d), which is novel, is described in particular:

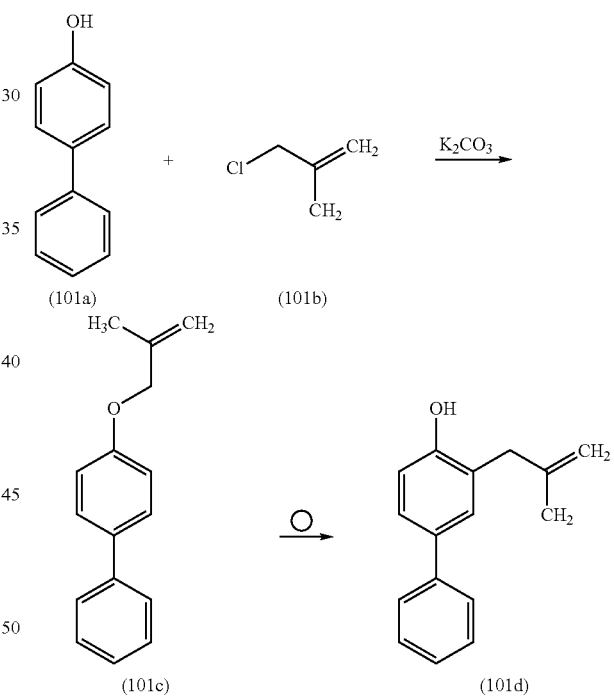

Example 1

Preparation of 4-biphenyl-methallyl Ether
(Compound of Formula 101c)

A mixture of 4.9 g (29 mmol) of 4-hydroxybiphenyl, 3.2 g (35 mmol) of methallyl chloride and 4.8 g (35 mmol) of anhydrous potassium carbonate in 100 ml of absolute DMF is stirred under nitrogen for 12 hours at 85° C. After filtration and removal of the solvent, the ether can be used without further purification for the subsequent rearrangement; yield 6.0 g (92% of theory).

Example 2

Preparation of 2-methallyl-4-phenyl-phenol (Compound of Formula 101d)

2.2 g (10 mmol) of the previously prepared ether are heated at reflux under nitrogen for 48 hours in 20 ml of o-dichlorobenzene at 180° C. The phenol is then separated from the unreacted ether by extracting the reaction mass, which has been diluted with 50 ml of methylene chloride, several times with sodium hydroxide solution at pH 11. After customary aqueous working-up, the product is obtained in sufficient purity for the subsequent hydrosilylation (>95 area % GC),
Yield 1.1 g (50% of theory)

$^1$H-NMR(CDCl$_3$):

6.8–7.45 (m,8H,arom.—H), 5.1 (s,1H,OH), 4.8/4.85 (s,1H, =CH), 3.35 (s,2H,CH$_2$), 1.7 (s,3H,CH$_3$)

Examples 3 to 6

Preparation of Further o-allylphenols

General Preparation of o-allylphenols in Diethylene Glycol Dimethyl Ether:

Approximately 25 mmol of the appropriate allyl phenyl ether are stirred in 10 ml of dry diethylene glycol dimethyl ether in a pressurised vessel for 12 hours at 220° C. The mixture is then diluted with approximately 40 ml of petroleum ether and washed twice with water. The isolated crude product is purified by distillation at 10$^{-2}$ mbar. The expected structures are confirmed by GC/MS and $^1$H-NMR.

| Compound of formula | Structure | Yield (% of theory) | $^1$H-NMR |
|---|---|---|---|
| (II) | 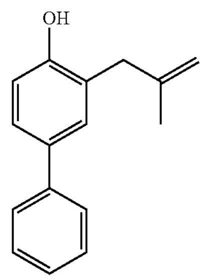 | 50 | (CDCl$_3$): 6.8–7.45 (m, 8H, arom.-H), 5.1 (s, 1H, OH), 4.8/4.85 (s, 1H, =CH), 3.35 (s, 2H, CH$_2$), 1.7 (s, 3H, CH$_3$) |
| (III) | 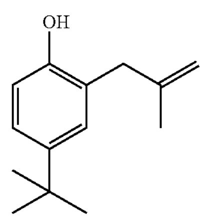 | 86 | (DMSO-d$_6$): 9.06(s, 1H, OH), 6.76–7.24(m, 3H, arom.-H), 4.72/4.82(s, 1H, =CH), 3.32(s, 2H, PhCH$_2$), 1.77(s, 3H, CH$_3$), 1.32(s, 9H, CCH$_3$) |
| (IV) | 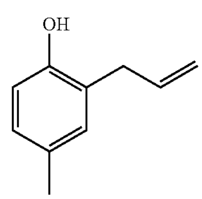 | 78 | (DMSO-d$_6$): 9.02(s, 1H, OH), 6.66–6.82 (m, 3H, arom.-H), 5.88–5.99(m, 1H, =CH), 4.98/5.02(dd, 2H, =CH$_2$), 3.24(d, 2H, PhCH$_2$), 2.16(s, 3H, CH$_3$) |
| (V) | 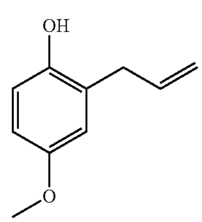 | 75 | (DMSO-d$_6$): 8.76(s, 1H, OH), 6.52–6.66 (m, 3H, arom.-H), 5.82–5.95(m, 1H, =CH), 4.93/4.97(dd, 2H, =CH$_2$), 3.58(s, 3H, CH$_3$), 3.19(d, 2H, PhCH$_2$) |

Examples 7 to 27

Hydrosilylation of o-allylphenols

According to the varying r activity of the types of silanes used, the hydrosilylations are carried out according to two similar procedures, which will be described hereinbelow by way of example. Yield and ¹H-NMR data are then given in Table form. With the exception of the compound of formula (106), all the compounds are novel.

Examples 7 to 23

Hydrosilylation of o-allylphenols in Toluene 2.9 mmol of the appropriate allylphenol are dissolved under nitrogen in 10 ml of absolute toluene together with a drop of Karstedt catalyst (platinum complex in divinyl-tetramethyl-disiloxane) and heated to 80° C. At that temperature, 3.5 mmol of the appropriate silane are added dropwise and then the mixture is stirred for a further 5 hours at that temperature. After cooling and removal of the solvent, finally under a high vacuum, the residue is purified by flash chromatography over silica gel (eluant: toluene). The products are obtained in the form of pale, viscous oils, and GC/MS and ¹H-NMR agree with the expected structures (Table 2):

TABLE 2

| Compound of formula | Structure | Yield (% of theory, based on phenol) | ¹H-NMR (CDCl₃) [ppm] |
|---|---|---|---|
| (101) | 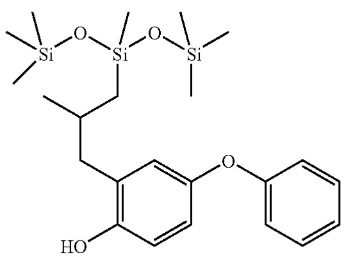 | 45% | 6.7–7.25(m, 8H, arom.-H), 4.9(s, 1H, OH), 2.55/2.25(dd, 1H, PhCH), 1.85(m, 1H, CH), 0.85(d, 3H, CH₃), 0.55/0.35(dd, 1H, SiCH), 0(s, 18H, SiCH₃), −0.1(s, 3H, SiCH₃) |
| (102) | 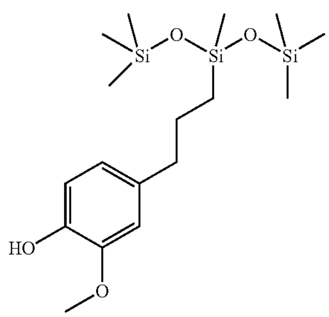 | 72% | 6.55–6.8(m, 3H, arom.-H), 5.35(s, 1H, OH), 3.8(s, 3H, OCH₃), 2.45(t, 2H, PhCH₂), 1.55(m, 2H, PhCH₂CH₂), 0.4(t, 2H, SiCH₂), 0.05(s, 18H, SiCH₃), −0.05(s, 3H, SiCH₃) |
| (103) | 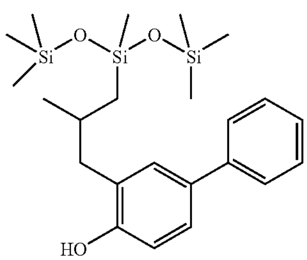 | 54% | 6.85–7.45(m, 8H, arom.-H), 5.0(s, 1H, OH), 2.65/2.35(dd, 1H, PhCH), 1.95(m, 1H, CH), 0.9(d, 3H, CH₃), 0.55/0.4(dd, 1H, SiCH), 0.05(s, 18H, SiCH₃), 0(s, 3H, SiCH₃) |
| (104) | 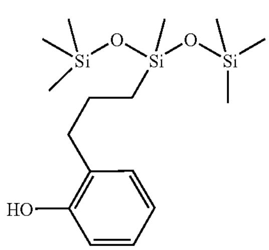 | 62% | 6.65–4.05(m, 4H, arom.-H), 4.15(s, 1H, OH), 2.5(t, 2H, PhCH₂), 1.55(m, 2H, CH₂CH₂CH₂), 0.45(t, 2H, SiCH₂), 0(s, 18H, SiCH₃), −0.1(s, 3H, SiCH₃) |
| (105) | 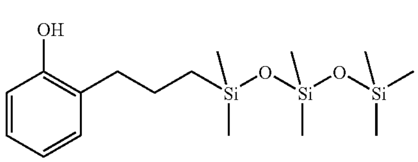 | 33% | 6.65–7.05(m, 4H, arom.-H), 4.65(s, 1H, OH), 2.5(t, 2H, PhCH₂), 1.6(m, 2H, CH₂CH₂CH₂), 0.55(t, 2H, CH₂Si), .05(s, 15H, SiCH₃), −0.05(s, 6H, SiCH₃) |

TABLE 2-continued

| Compound of formula | Structure | Yield (% of theory, based on phenol) | ¹H-NMR (CDCl₃) [ppm] |
|---|---|---|---|
| (106) | 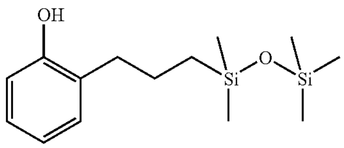 | 34% | 6.7–7.25(m, 4H, arom.-H), .65(s, 1H, OH), 2.55(t, 2H, PhCH₂), 1.6(m, 2H, CH₂CH₂CH₂), 0.55(t, 2H, CH₂Si), 0(s, 15H, SiCH₃) |
| (107) | 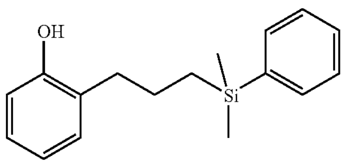 | 52% | 6.65–7.5(m, 9H, arom.-H), 4.5(s, 1H, OH), 2.5(t, 2H, PhCH₂), 1.55(m, 2H, CH₂CH₂CH₂), 0.85(t, 2H, CH₂Si), 0.2(s, 6H, SiCH₃) |
| (108) | 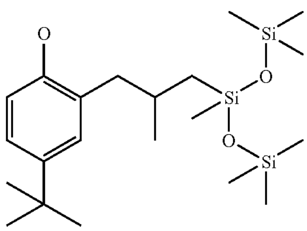 | 61% | ¹H-NMR(DMSO-d₆): 8.81(s, 1H, OH), 6.61–6.93(m, 3H, arom. H), 2.37(d, 2H, PhCH₂), 1.87(m, 1H, CH), 1.18(s, 9H, C(CH₃)₃), 0.82(d, 3H,CH₃), 0.57/0.27(dd, 1H, SiCH), 0(s, 18H, SiCH₃), −0.07(s, 3H, SiCH₃) 13C ok |
| (109) | 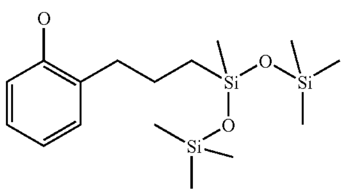 | 88% | ¹H-NMR(DMSO-d₆): 8.81(s, 1H, OH), 6.56–6.72(m, 3H, arom.-H), 2.4(t, 2H, PhCH₂), 2.08(s, 3H, CH₃), 1.46(m, 2H, CH₂CH₂), 0.40(t, 2H, CH₂Si), 0(s, 18H, Si(CH₃)₃), −0.08(s, 3H, SiCH₃) 13C ok |
| (110) | 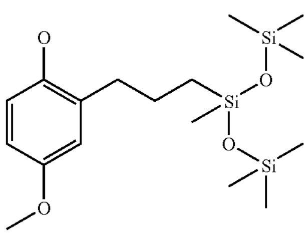 | 51% | ¹H-NMR(DMSO-d₆): 8.62(s, 1H, OH), 6.45–6.65(m, 3H, arom.-H), 3.57(s, 3H, OCH₃), 2.42(t, 2H, PhCH₂), 1.47(m, 2H, CH₂CH₂), 0.40(t, 2H, CH₂Si), 0(s, 18h, Si(CH₃)₃), −0.08(s, 3H, SiCH₃) 13C ok |
| (111) | 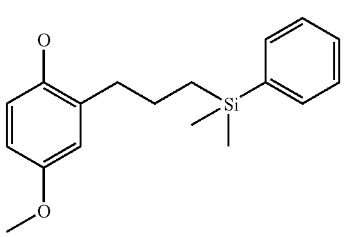 | 42% | ¹H-NMR(DMSO-d₆): 8.44(s, 1H, OH), 6.30–7.30(m, 8H, arom.-H), 3.40(s, 3H, OCH₃), 2.26(t, 2H, PhCH₂), 1.30(m, 2H, CH₂CH₂), 0.53(t, 2H, CH₂Si), 0(s, 6H, SiCH₃) 13C ok |
| (112) | 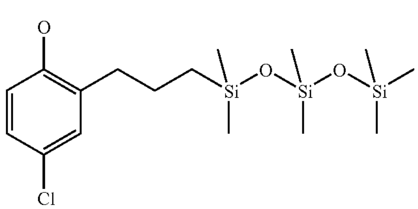 | 30% | ¹H-NMR(DMSO-d₆): 9.43(s, 1H, OH), 6.68–6.98(m, 3H, arom.-H), 2.46(t, 2H, PhCH₂), 1.50(m, 2H, CH₂CH₂), 0.49(t, 2H, CH₂Si), 0(s, 15H, SiCH₃, −0.06(s, 6H, SiCH₃) 13C ok |

TABLE 2-continued

| Compound of formula | Structure | Yield (% of theory, based on phenol) | ¹H-NMR (CDCl₃) [ppm] |
|---|---|---|---|
| (113) | 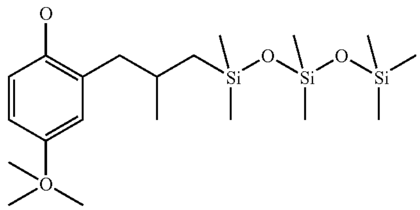 | 42% | ¹H-NMR(DMSO-d₆): 8.81(s, 1H, OH), 6.59–6.92(m, 3H, arom.-H), 2.29/2.44 (dd, 1H, PhCH), 1.89(m, 1H, CH₃CH), 1.16(s, 9H, C(CH₃)₃), 0.81(d, 3H, CHCH₃), 0.39/0.62(dd, 1H, CHSi), 0(s, 15H, SiCH₃), −0.08(s, 6H, SiCH₃) 13C ok |
| (114) | 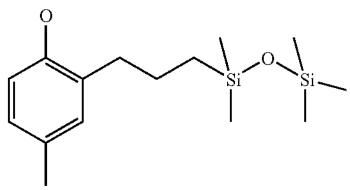 | 53% | ¹H-NMR(DMSO-d₆): 8.83(s, 1H, OH), 6.58–6.76(m, 3H, arom.-H), 2.43(t, 2H, PhCH₂), 2.10(s, 3H, CH₃), 1.48(m, 2H, CH₂CH₂), 0.49(t, 2H, CH₂Si), 0(s, 9H, SiCH₃), −0.01 (s, 6H, SiCH₃) 13C ok |
| (115) | 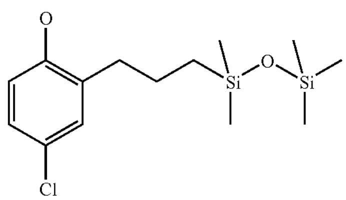 | 70% | ¹H-NMR(DMSO-d₆): 9.46(s, 1H, OH), 6.67–7.04(m, 3H, arom.-H), 2.47(t, 2H, PhCH₂), 1.50(m, 2H, CH₂CH₂), 0.48(t, 2H, CH₂Si), 0(s, 9H, SiCH₃), −0.01(s, 6H, SiCH₃) 13C ok |
| (116) | 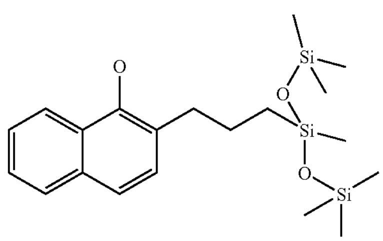 | 65% | ¹H-NMR/DMSO-d₆): 8.85(s, 1H, OH), 7.1–8.15(m, 6H, arom.-H), 2.75(t, 2H, PhCH₂), 1.55(m, 2H, CH₂CH₂), 0.45(t, 2H, CH₂Si), 0(s, 18H, SiCH₃), −0.1(s, 3H, SiCH₃) |
| (117) | 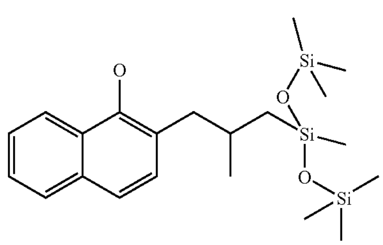 | 75% | ¹H-NMR(DMSO-d₆): 8.85(s, 1H, OH), 7.1–8.15(m, 6H, arom.-H), 2.6(d, 2H, PhCH₂), 1.95(m, 1H, CH), 0.85(d, 3H, CH₃), 0.6/0.35 (dd, 1H, SiCH), 0(s, 18H, SiCH₃), −0.1 (s, 3H, SiCH₃) |

Examples 24 to 27

Hydrosilylation of o-allylphenols in Xylene 2.9 mmol of the appropriate allylphenol are dissolved under nitrogen in 10 ml of absolute xylene together with a drop of Karstedt catalyst (platinum complex in divinyl-tetramethyl-disiloxane) and 3.5 mmol of the appropriate silane. The reaction mixture is maintained at reflux for 48 hours. After cooling and removal of the solvent, finally under a high vacuum, the residue is purified by flash chromatography over silica gel (eluant: xylene). The products are obtained in the form of pale, viscous oils, and GC/MS and ¹H-NMR agree with the expected structures (Table 3):

TABLE 3

| Compound of formula | Structure | Yield (% of theory, based on phenol) | $^1$H-NMR (CDCl$_3$) [ppm] |
|---|---|---|---|
| (118) | triethylsilyl-CH$_2$-CH(CH$_3$)-CH$_2$- attached to 2-position of 4-phenoxyphenol | 41% | — |
| (119) | 2-[3-(phenyldimethylsilyl)propyl]-4-chlorophenol | 29% | $^1$H-NMR(CDCl$_3$): 6.48–7.34(m, 8H, arom.-H), 4.42(s, 1H, OH), 2.39(t, 2H, PhCH$_2$), 1.45 (m, 2H, CH$_2$CH$_2$CH$_2$), 0.65(t, 2H, CH$_2$Si), 0.1 (s, 6H, SiCH$_3$) 13C ok |
| (120) | 2-[2-methyl-3-(phenyldimethylsilyl)propyl]-4-phenoxyphenol | 25% | $^1$H-NMR(DMSO-d$_6$): 8.94(s, 1H, OH), 6.41–7.22(m, 13H, arom.-H). 2.09/2.24 (dd, 1H, PhCH), 1.69(m, 1H, CH$_3$CH), 0.56 (d, 3H, CH$_3$), 0.40/0.65(dd, 1H, CHSi), 0(s, 6H, SiCH$_3$) 13C ok |
| (121) | 2-[2-methyl-3-(phenyldimethylsilyl)propyl]-1-naphthol | 37% | $^1$H-NMR(DMSO-d$_6$): 8.65(s, 1H, OH), 6.8–7.95(m, 11H, arom.-H), 2.45/2.35 (dd, 1H, PhCH), 1.75(m, 1H, CH), 0.75/0.45(dd, 1H, CHSi), 0.6(d, 3H, CH$_3$), 0(s, 6H, SiCH$_3$) |

Example 28

Determination of the Minimum Inhibitory Concentration (MIC) in the Agar Incorporation Test (MIC Test)

| | |
|---|---|
| Medium: | casein/soybean flour peptone agar (Merck) *Sabouraud 4% glucose agar (Merck) |
| Dilution medium: | sterile 0.85% NaCl solution |
| Test organisms: | Staphylococcus aureus ATCC 9144 Escherichia coli NCTC 8196 Pseudomonas aeruginosa CIP A-22 Candida albicans ATCC 10231 *Aspergillus niger ATCC 6275 |
| Incubation: | 24 hours at 37° C. *3 days at 28° C. |
| Test solution: | 1% stock solutions of all the test substances in a suitable solvent are prepared and diluted in serial dilutions to final concentrations of from 1000 ppm to 10 ppm. |

Test Principle:

0.3 ml of each dilution stage is mixed with 15 ml of still-liquid nutrient medium. After the nutrient medium has solidified, 10 µl of each of the following organism dilutions of the test strains in 0.85% NaCl solution are spotted onto the agar medium:

| | |
|---|---|
| Staphylococcus aureus ATCC 9144 | 1:100 dilution |
| Escherichia coli NCTC 8196 | 1:1000 dilution |
| Pseudomonas aeruginosa CIP A-22 | 1:1000 dilution |
| Candida albicans ATCC 10231 | 1:10 dilution |
| Aspergillus niger ATCC 6275 | 1:10 dilution |

The plates are incubated for 24 hours at 37° C. (A. niger 3 days at 28° C.) and then the highest dilution (lowest concentration) of the test substance at which growth is just no longer discernible (corresponds to the MIC) is determined.

The results are shown in Tables 3a and 3b.

TABLE 3a

MIC values in ppm

| Microorganisms | Compound of formula | | | |
|---|---|---|---|---|
| | (101) | (102) | (118) | (104) |
| Staphylococcus aureus ATCC 9144 | 1000 | >1000 | 4 | 8 |
| Escherichia coli NCTC 8196 | >1000 | >1000 | >1000 | >1000 |
| Pseudomonas aeruginosa CIP A-22 | >1000 | >1000 | >1000 | >1000 |
| Candida albicans ATCC 10231 | >1000 | >1000 | >1000 | >1000 |
| Aspergillus niger ATCC 6275 | >1000 | >1000 | >1000 | >1000 |

TABLE 3b

MIC values in ppm

| Microorganisms | Compound of formula | | | |
|---|---|---|---|---|
| | (103) | (105) | (107) | (106) |
| Staphylococcus aureus ATCC 9144 | >560 | 15.6 | 1.9 | 7.8 |
| Staphylococcus hominis DSM 20328 | >560 | >1000 | 7.8 | 31.2 |
| Corynebacterium xerosis ATCC 373 | 17.5 | 3.9 | 1.9 | 7.8 |
| Enterococcus hirae ATCC 10541 | >560 | 15.6 | 3.9 | 15.6 |
| Escherichia coli NCTC 8196 | >560 | >1000 | >1000 | >1000 |
| Pseudomonas aeruginosa CIP A-22 | >560 | >1000 | >1000 | >1000 |
| Candida albicans ATCC 10231 | >560 | >1000 | 125 | >1000 |
| Aspergillus niger ATCC 6275 | >560 | >1000 | 15.6 | 31.2 |

TABLE 3c

MIC values in ppm

| Microorganisms | Compound of formula | | | | |
|---|---|---|---|---|---|
| | (108) | (109) | (110) | (119) | (111) |
| Staphylococcus aureus ATCC 9144 | 0 | 15 | 250 | 4 | 125 |
| Corynebacterium xerosis ATCC 373 | 8 | 4 | 4 | 2 | 8 |
| Escherichia coli NCTC 8196 | >1000 | >1000 | >1000 | >1000 | >1000 |
| Pseudomonas aeruginosa CIP A-22 | >1000 | >1000 | >1000 | >1000 | >1000 |
| Candida albicans ATCC 10231 | >1000 | >1000 | >1000 | 62 | >1000 |
| Aspergillus niger ATCC 6275 | >1000 | >1000 | >1000 | 62 | >1000 |

TABLE 3d

MIC values in ppm

| Microorganisms | Compound of formula | | | | |
|---|---|---|---|---|---|
| | (112) | (120) | (113) | (114) | (115) |
| Staphylococcus aureus ATCC 9144 | 7 | 8 | >1000 | 8 | 15 |
| Corynebacterium xerosis ATCC 373 | 2 | 4 | 62 | 8 | 8 |
| Escherichia coli NCTC 8196 | >1000 | >1000 | >1000 | >1000 | 250 |
| Pseudomonas aeruginosa CIP A-22 | >1000 | >1000 | >1000 | >1000 | >1000 |
| Candida albicans ATCC 10231 | >1000 | >1000 | >1000 | >1000 | 500 |
| Aspergillus niger ATCC 6275 | >1000 | >1000 | >1000 | >1000 | 500 |

TABLE 3e

MIC values in ppm

| Microorganisms | Compound of formula | | |
|---|---|---|---|
| | (121) | (116) | (117) |
| Staphylococcus aureus ATCC 9144 | >1000 | >1000 | >1000 |
| Staphylococcus hominis DSM 20328 | >1000 | >1000 | >1000 |
| Corynebacterium xerosis ATCC 373 | 250 | 500 | 1000 |
| Escherichia coli ATCC 10536 | >1000 | >1000 | >1000 |
| Candida albicans ATCC 1023 | >1000 | >1000 | >1000 |
| Aspergillus niger ATCC 6275 | >1000 | >1000 | >1000 |

The results show a strong antimicrobial activity of the test substances against Gram-positive and Gram-negative bacteria and against fungi and yeasts.

What is claimed is:

1. A process for the preparation of a compound of formula

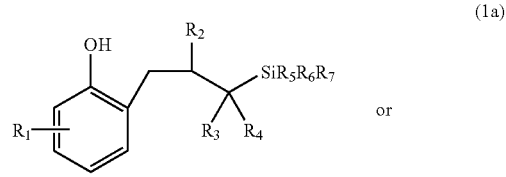

(1a)

or

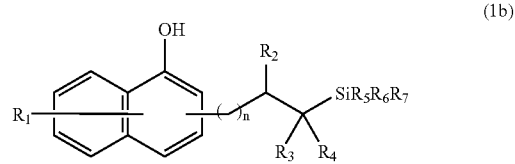

(1b)

wherein a phenol or naphthol compound is etherified with an allyl halide (1st step), the resulting alkenyl phenyl ether compound is rearranged to form an alkenylphenyl compound (2nd step), and a silane compound that contains at least one Si—H bond is added to that compound according to the following Scheme:

1st step:

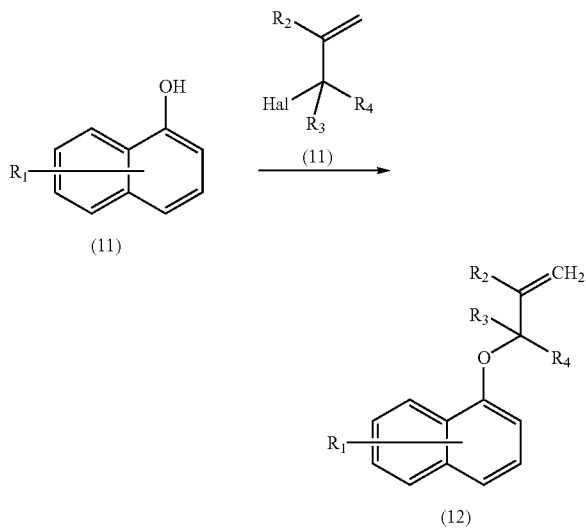

2nd step:

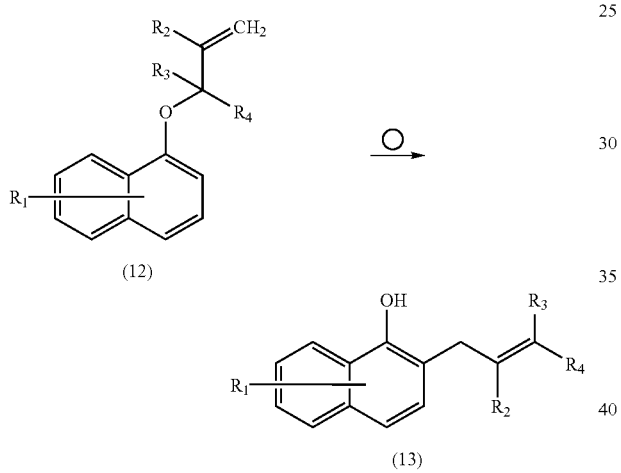

3rd step:

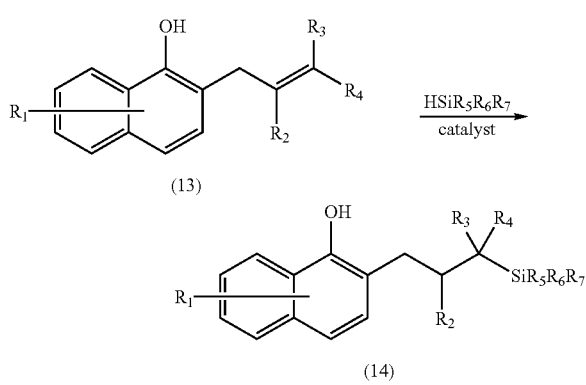

wherein
R$_1$ is hydrogen; halogen; hydroxy; C$_1$–C$_{20}$alkyl; C$_3$–C$_{12}$cycloalkyl; C$_1$–C$_{20}$alkoxy; trifluoromethyl; pentafluoroethyl; mono- or di-C$_1$–C$_5$alkylamino; hydroxy-C$_1$–C$_5$alkyl; or phenyl, phenyl-C$_1$–C$_{20}$alkyl, phenoxy, phenyl-C$_1$–C$_{20}$alkoxy, naphthyl or naphthyl-C$_1$–C$_{20}$alkyl each unsubstituted or substituted by C$_1$–C$_5$alkyl, C$_3$–C$_{12}$cycloalkyl, C$_1$–C$_5$alkoxy, C$_3$–C$_{12}$cycloalkoxy, halogen, oxo, carboxy, carboxy-C$_1$–C$_7$alkyl ester, carboxy-C$_3$–C$_{12}$cycloalkyl ester, cyano, trifluoromethyl, pentafluoroethyl, amino N,N-mono- or di-C$_1$–C$_{20}$alkylamino or by nitro;

R$_2$, R$_3$ and R$_4$ are each independently of the others hydrogen; C$_1$–C$_{20}$alkyl; or C$_3$–C$_{12}$-cycloalkyl;

R$_5$, R$_6$ and R$_7$ are each independently of the others C$_1$–C$_{20}$alkyl; C$_5$–C$_{10}$aryl; C$_1$–C$_{20}$alkoxy; phenyl-C$_1$–C$_{20}$alkyl; phenyl-C$_1$–C$_{20}$alkoxy, C$_2$–C$_5$alkenyl; —O—Si—(C$_1$–C$_5$alkyl)$_3$; or —O—Si—(C$_1$–C$_5$alkyl)$_2$-O—Si(C$_1$–C$_5$alkyl)$_3$ and n is 0 or 1, there not being included compounds of formula (1a) wherein R$_1$, R$_2$, R$_3$ and R$_4$ are hydrogen and R$_5$, R$_6$ and R$_7$ are simultaneously methyl or ethyl.

2. A method for the antimicrobial treatment of a surface, which comprises contacting said surface with an antimicrobially effective amount of a silanyl phenol or naphthol compound of formula

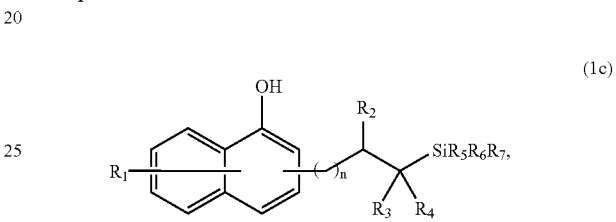

(1c)

wherein
R$_1$ is hydrogen; halogen; hydroxy; C$_1$–C$_{20}$alkyl; C$_3$–C$_{12}$cycloalkyl; C$_1$–C$_{20}$alkoxy; trifluoromethyl; pentafluoroethyl; mono- or di-C$_1$–C$_5$alkylamino; hydroxy-C$_1$–C$_5$alkyl; or phenyl, phenyl-C$_1$–C$_{20}$alkyl, phenoxy, phenyl-C$_1$–C$_{20}$alkoxy, naphthyl or naphthyl-C$_1$–C$_{20}$alkyl each unsubstituted or substituted by C$_1$–C$_5$alkyl, C$_3$–C$_{12}$cycloalkyl, C$_1$–C$_5$alkoxy, C$_3$–C$_{12}$cycloalkoxy, halogen, oxo, carboxy, carboxy-C$_1$–C$_7$alkyl ester, carboxy-C$_3$–C$_{12}$cycloalkyl ester, cyano, trifluoromethyl, pentafluoroethyl, amino, N,N-mono- or di-C$_1$–C$_{20}$alkylamino or by nitro;

R$_2$, R$_3$ and R$_4$ are each independently of the others hydrogen; C$_1$–C$_{20}$alkyl; or C$_3$–C$_{12}$-cycloalkyl;

R$_5$, R$_6$ and R$_7$ are each independently of the others C$_1$–C$_{20}$alkyl; C$_5$–C$_{10}$aryl; C$_1$–C$_{20}$alkoxy; phenyl-C$_1$–C$_{20}$alkyl; phenyl-C$_1$–C$_{20}$alkoxy; C$_2$–C$_5$alkenyl; —O—Si—(C$_1$–C$_5$alkyl)$_3$; or —O—Si—(C$_1$–C$_5$alkyl)$_2$-O—Si(C$_1$–C$_5$alkyl)$_3$; and n is 0 or 1.

3. A method according to claim 2, wherein the compound of formula (1c) is used in the antimicrobial treatment, deodorisation and disinfection of the skin, mucosa and hair.

4. A method according to claim 2, wherein the compound of formula (1c) is used in the treatment of textile fibre materials.

5. A method according to claim 2, wherein the compound of formula (1c) is used in preservation.

6. A method according to claim 2, wherein the compound of formula (1c) is used in washing and cleaning formulations.

7. A method according to claim 2, wherein the compound of formula (1c) is used in imparting antimicrobial properties to and preserving plastics, paper, nonwoyens, wood or leather.

8. A method according to claim 2, wherein the compound of formula (1c) is used in imparting antimicrobial properties to and preserving technical products.

9. A method according to claim 2, wherein the compound of formula (1c) is used as a biocide in technical processes.

10. A personal care preparation, comprising from 0.01 to 15% by weight, based on the total weight of the composition, of the compound of formula (1c) defined according to claim 2, and cosmetically tolerable adjuvants.

11. An oral composition, comprising from 0.01 to 15% by weight, based on the total weight of the composition, of the compound of formula (1c) defined according to claim 2, and orally tolerable adjuvants.

* * * * *